US010323051B2

(12) United States Patent
Woodward et al.

(10) Patent No.: US 10,323,051 B2
(45) Date of Patent: Jun. 18, 2019

(54) METHODS FOR CONTROLLING DEPOLYMERIZATION OF POLYMER COMPOSITIONS

(75) Inventors: Gary Woodward, Northwich (GB); Subramanian Kesavan, East Windsor, NJ (US); Adedamola Adedeji, Carteret, NJ (US); Timothy Curtis, East Windsor, NJ (US)

(73) Assignee: RHODIA OPERATIONS, Paris (FR)

( * ) Notice: Subject to any disclaimer, the term of this patent is extended or adjusted under 35 U.S.C. 154(b) by 639 days.

(21) Appl. No.: 13/467,272

(22) Filed: May 9, 2012

(65) Prior Publication Data

US 2012/0289436 A1 Nov. 15, 2012

Related U.S. Application Data

(60) Provisional application No. 61/518,642, filed on May 9, 2011, provisional application No. 61/574,774, filed on Aug. 9, 2011.

(51) Int. Cl.
*C07F 9/54* (2006.01)
*C09K 8/60* (2006.01)
*C09K 8/68* (2006.01)
*A01N 25/00* (2006.01)
*A01N 57/34* (2006.01)
*C09K 8/035* (2006.01)

(52) U.S. Cl.
CPC ............ *C07F 9/5407* (2013.01); *A01N 25/00* (2013.01); *C09K 8/035* (2013.01); *C09K 8/605* (2013.01); *C09K 8/68* (2013.01)

(58) Field of Classification Search
CPC ....... A01N 25/00; A01N 57/34; C07F 9/5407; C09K 8/035; C09K 8/605; C09K 8/68
See application file for complete search history.

(56) References Cited

U.S. PATENT DOCUMENTS

| 3,240,737 | A |  | 3/1966 | McKennon |
| 4,331,543 | A | * | 5/1982 | Wilson ................ C09K 8/584 166/275 |
| 5,385,896 | A | * | 1/1995 | Bryan ................... A01N 57/34 514/129 |

(Continued)

FOREIGN PATENT DOCUMENTS

GB 654026 5/1951

OTHER PUBLICATIONS

Jennifer Moore, et al, "Compatibility of Tetrakis(Hydroxymethyl) Phosphonium Sulfate (THPS) and Ammonium Bisulfite (ABS)", NACE Intl, Corrosion 2010 Conference & Expo, Paper No. 10407, pp. 1-14.

(Continued)

*Primary Examiner* — Alicia Bland

(57) ABSTRACT

A method of controlling or arresting the rate of depolymerization of a polymer composition during a biocide treatment, and use of such methods in oilfield and industrial applications. Also disclosed are methods of preparing a visco-stable application fluid containing a biocide in an amount effective to reduce bacteria count, as well as additive compositions capable of reducing bacteria count in application fluids while maintaining viscosity in such fluids. Also disclosed are methods of preparing biocide-containing application fluids with improved friction reducing properties, as well as related compositions.

2 Claims, 1 Drawing Sheet

| THPS (ppm) | Polymer (% w/w) | Inhibitor (ppm) | Initial pH of polymer | pH after Buffer | pH after inhibitor | Visc (cP) t=0 min | Visc (cP) t=1 min | Visc (cP) t=2 mins | Visc (cP) t=5 mins | Visc (cP) t=10 mins | Visc (cP) t=15 mins | Visc (cP) t=20 mins | Visc (cP) t=30 mins | Visc (cP) t=45 mins | Visc (cP) t=60 mins | Visc (cP) t=24 hours |
|---|---|---|---|---|---|---|---|---|---|---|---|---|---|---|---|---|
| 0.5 | 1% pol A | 0 | 5.4 | 4.1 |  | 23.9 | 22.7 | 22.6 | 22.9 | 22.7 | 22.8 |  | 22.8 | 22.7 | 22.6 |  |
| 25 | 1% pol A | 0 | 5.4 | 4.1 |  | 23.9 | 23.5 | 23.5 | 23.3 |  | 22.8 |  | 21.9 | 21.2 | 20.9 |  |
| 50 | 1% pol A | 0 | 4.8 | 4.1 |  | 23.8 | 21 |  |  | 15 |  |  | 11.1 | 10 | 9.7 |  |
| 75 | 1% pol A | 0 | 4.6 | 4 |  | 23.8 | 18 |  | 14.3 |  | 9.5 |  |  | 7.4 | 7.3 |  |
| 100 | 1% pol A | 0 | 4.5 | 3.9 |  | 23.8 |  | 13 | 6.9 | 5.1 |  | 4.7 | 4.4 | 4.1 | 3.9 |  |
| 125 | 1% pol A | 0 | 4.8 | 4.1 |  | 23.8 | 10.2 | 9.5 | 6.2 |  | 2.3 |  | 2.2 | 2.1 | 2 |  |
| 75 | 1% pol A | hydroquinone 25ppm | 4.6 | 3.9 | 3.9 | 23.8 | 22.5 |  | 21.8 | 20.3 | 19.7 |  | 17.1 | 15.9 | 14.6 |  |
| 75 | 1% pol A | hydroquinone 50ppm | 4.5 | 3.9 | 3.9 | 25.1 | 23.2 |  | 22.6 | 22.3 | 21 |  | 19.3 | 17.5 | 17.1 |  |
| 175 | 1% pol A | Ascorbic acid 100ppm | 4.8 | 4 | 3.9 | 27.5 | 26.9 |  | 27.1 |  | 27.2 |  | 26.8 | 26.5 | 26.5 |  |
| 75 | 1% pol A | Ascorbic acid 100ppm | 4.7 | 4 | 3.9 | 27.5 |  | 26.2 | 26.3 |  | 26.2 |  | 26.1 | 25.9 | 25.9 | 24.5 |
| 75 | 1% pol A | Ascorbic acid 50ppm | 4.8 | 4.3 | 4.3 | 24.9 |  | 25.2 | 25.1 |  | 24.6 |  | 24.2 | 23.6 | 22.8 |  |
| 75 | 1% pol A | Ascorbic acid 10ppm | 4.6 | 4.4 | 4.3 | 24.9 | 24.9 |  |  |  |  | 24.7 (19min) | 24.2 | 23.3 | 23 |  |
| 75 | 1% pol A | Ascorbic acid 1ppm | 4.6 | 3.9 | 3.8 | 24.9 | 24.9 | 24.9 |  | 24.5 |  |  | 24.3 | 24 | 23.1 |  |
| 75 | 1% pol A | Ascorbic acid 0.1ppm | 4.8 | 4.1 | 3.8 | 24.3 |  |  |  |  |  |  |  |  | 22.7 |  |
| 75 | 1% pol A | Ascorbic acid 0.01ppm | 4.8 | 4 | 3.9 | 24.3 |  |  |  |  |  |  |  |  | 4.9 |  |
| 75 | 1% pol B | 0 | 4 | 3.9 |  | 47.4 | 43.2 |  | 36.5 |  | 23.8 |  | 18.8 | 15.6 | 14.5 |  |
| 75 | 1% pol B | Ascorbic acid 100ppm | 4.6 | 4 | 3.9 | 47.4 |  | 46.3 | 46.4 (6mins) |  | 46.6 |  | 46.6 | 46.6 | 46.3 |  |

(56) References Cited

U.S. PATENT DOCUMENTS

| | | | |
|---|---|---|---|
| 5,741,757 A * | 4/1998 | Cooper | A01N 57/20 |
| | | | 504/153 |
| 6,884,884 B2 | 4/2005 | Magallanes et al. | |
| 7,572,757 B1 | 8/2009 | Gupta et al. | |
| 2006/0180789 A1 | 8/2006 | Jones et al. | |
| 2009/0324820 A1 | 12/2009 | Chartier | |
| 2010/0190666 A1 | 7/2010 | Ali et al. | |
| 2010/0204068 A1 | 8/2010 | Kesavan et al. | |
| 2010/0218950 A1 | 9/2010 | Starkey, II et al. | |
| 2010/0307757 A1 | 12/2010 | Blow et al. | |
| 2011/0071058 A1 | 3/2011 | Howard et al. | |
| 2012/0034313 A1 * | 2/2012 | Wrangham | A01N 35/06 |
| | | | 424/607 |
| 2012/0152149 A1 * | 6/2012 | Mijolovic | A01N 31/02 |
| | | | 106/15.05 |

OTHER PUBLICATIONS

Carl Aften, et al, "Critical Evaluation of Biocide-Friction Reducer Interactions Used in Slickwater Fracs", SPE Intl, SPE 141358, pp. 1-21.

* cited by examiner

| THPS (ppm) | Polymer (% w/w) | Inhibitor (ppm) | Initial pH of polymer | pH after Buffer | pH after inhibitor | Visc (cP) t=0 min | Visc (cP) t=1 min | Visc (cP) t=2 mins | Visc (cP) t=5 mins | Visc (cP) t=10 mins | Visc (cP) t=15 mins | Visc (cP) t=20 mins | Visc (cP) t=30 mins | Visc (cP) t=45 mins | Visc (cP) t=60 mins | Visc (cP) t=24 hours |
|---|---|---|---|---|---|---|---|---|---|---|---|---|---|---|---|---|
| 0.5 | 1% pol A | 0 | 5.4 | 4.1 | | 23.9 | 22.7 | 22.6 | 22.9 | 22.7 | 22.8 | | 22.8 | 22.7 | 22.6 | |
| 25 | 1% pol A | 0 | 5.4 | 4.1 | | 23.9 | 23.5 | 23.5 | 23.3 | | 22.8 | | 21.9 | 21.2 | 20.9 | |
| 50 | 1% pol A | 0 | 4.8 | 4.1 | | 23.8 | 21 | | | 15 | | | 11.1 | 10 | 9.7 | |
| 75 | 1% pol A | 0 | 4.6 | 4 | | 23.8 | 18 | | 14.3 | | 9.5 | | | 7.4 | 7.3 | |
| 100 | 1% pol A | 0 | 4.5 | 3.9 | | 23.8 | | 13 | 6.9 | 5.1 | | 4.7 | 4.4 | 4.1 | 3.9 | |
| 125 | 1% pol A | 0 | 4.8 | 4.1 | | 23.8 | 10.2 | 9.5 | 6.2 | | 2.3 | | 2.2 | 2.1 | 2 | |
| 75 | 1% pol A | hydroquinone 25ppm | 4.6 | 3.9 | 3.9 | 23.8 | 22.5 | | 21.8 | 20.3 | 19.7 | | 17.1 | 15.9 | 14.6 | |
| 75 | 1% pol A | hydroquinone 50ppm | 4.5 | 3.9 | 3.9 | 25.1 | 23.2 | | 22.6 | 22.3 | 21 | | 19.3 | 17.5 | 17.1 | |
| 175 | 1% pol A | Ascorbic acid 100ppm | 4.8 | 4 | 3.9 | 27.5 | 26.9 | | 27.1 | | 27.2 | | 26.8 | 26.5 | 26.5 | 24.5 |
| 75 | 1% pol A | Ascorbic acid 100ppm | 4.7 | 4 | 3.9 | 27.5 | | 26.2 | 26.3 | | 26.2 | | 26.1 | 25.9 | 25.9 | |
| 75 | 1% pol A | Ascorbic acid 50ppm | 4.8 | 4.3 | 4.3 | 24.9 | | 25.2 | 25.1 | | 24.6 | 24.7 (19min) | 24.2 | 23.6 | 22.8 | |
| 75 | 1% pol A | Ascorbic acid 10ppm | 4.6 | 4.4 | 4.3 | 24.9 | | 24.9 | | | | | 24.2 | 23.3 | 23 | |
| 75 | 1% pol A | Ascorbic acid 1ppm | 4.6 | 3.9 | 3.8 | 24.9 | | 24.9 | 24.9 | | 24.5 | | 24.3 | 24 | 23.1 | |
| 75 | 1% pol A | Ascorbic acid 0.1ppm | 4.8 | 4.1 | 3.8 | 24.3 | | | | | | | | | 22.7 | |
| 75 | 1% pol A | Ascorbic acid 0.01ppm | 4.8 | 4 | 3.9 | 24.3 | | | | | | | | | 4.9 | |
| 75 | 1% pol B | 0 | 4 | 3.9 | | 47.4 | 43.2 | | 36.5 | | 23.8 | | 18.8 | 15.6 | 14.5 | |
| 75 | 1% pol B | Ascorbic acid 100ppm | 4.6 | 4 | 3.9 | 47.4 | | 46.3 | 46.4 (6mins) | | 46.6 | | 46.6 | 46.6 | 46.3 | | ns
METHODS FOR CONTROLLING DEPOLYMERIZATION OF POLYMER COMPOSITIONS

CROSS-REFERENCE TO RELATED APPLICATIONS

This application claims the benefit of U.S. Provisional Application Ser. No. 61/518,642 filed May 9, 2011, as well as U.S. Provisional Application Ser. No. 61/574,774 filed Aug. 9, 2011, both herein incorporated by reference.

FIELD OF THE INVENTION

This invention relates to methods of controlling or arresting depolymerization of polymer and polymer compositions, and in particular, to methods of controlling or arresting depolymerization of polymer compositions in industrial and oil well applications and the preparation of visco-stable application fluids.

BACKGROUND OF THE INVENTION

Bacterial contamination of industrial applications (e.g., drilling fluids such as fracturing fluids or in water injection systems) is a source of problems. For example, microorganisms in oilfields, in injection water or industrial applications where water is collected from ponds or similar water sources may include iron-oxidizing bacteria, sulfate-reducing bacteria, slime-forming bacteria, sulfide oxidizing bacteria, yeast and molds, and protozoa.

Some industrially utilized fluids contain natural or synthetic polymers in their formulation that provide a food source for bacterial populations. Bacterial growth can result in souring of the crude oil in a reservoir, which is caused by the reduction of inorganic sulfate compounds to sulfides by certain bacteria. Bacterial metabolism can generate deleterious products, for example, hydrogen sulfide that aside from being a toxic gas can lead to decomposition of mud polymers, formation of problematic solids, such as iron sulfide, and/or corrosive action on drilling tubes and drilling hardware.

U.S. Pat. No. 3,240,737 discusses degradation of polyacrylamide and other water soluble polymers using ferrous salts and a ferric ion chelating agent in an oxygenated system. U.S. Pat. No. 6,884,884 to Magallanes et al. discusses the depolymerization of polymers and in particular, polysaccharides.

SUMMARY OF THE INVENTION

Biocides are used to treat water and destroy bacteria or a substantial amount of bacteria during a biocide treatment. This is especially important when the water source is from a pond, lake, pit or produced water from an oil well etc. Several biocides such as glutaraldehyde, tetrakis(hydroxymethyl)phosphonium sulfate ("THPS"), etc. can be used to destroy bacteria present in such source water.

When THPS is used as biocide in aerobic oilfield application fluids such as fracturing fluids or slickwater fluids, it is recognized problem that there is a significant decrease in the viscosity of the fluid which takes place at ambient temperatures.

"Oilfield application fluid" means any fluid utilized in the processing, extraction or treatment of oil, typically as a well treatment fluid, coiled tubing fluid, drilling fluid, completion fluid, fracturing fluid, stimulation fluid, or slickwater fluid, sand control fluid, cementing process/operations fluid, fracturing pit fluid, water injector fluid, flooding fluid (including, for example, in improving oil recovery (IOR) polymer flooding or in enhanced oil recovery (EOR) polymer flooding, among others) or any other fluid that is introduced into an underground formation and utilized (either directly or indirectly) in the recovery of hydrocarbons. The fluid can be introduced in any number of ways, typically by fracturing equipment, drilling equipment, coiled tubing equipment, cementing equipment, or water injectors.

Similarly, application fluids can include industrial application fluids which can be, for example, systems used in water purification, heating and cooling, papermaking, metalworking, pulpmaking, storage, and cleaning and rinsing processes, among others.

Typically, well treatment fluids contain a polysaccharide, mainly guar or guar derivatives, or other polymers such as polyacrylamide. It would be desirable to use THPS as a biocide and still maintain the viscosity of the treatment fluid It is also desirable to be able to control depolymerization of polymer compositions, including polysaccharide compositions, in industrial applications including but not limited to oilfield, well, slickwater, paper processing, water processing, and other industrial applications. Depending on the application, the depolymerization (decrease in molecular weight) manifests itself as a decrease in viscosity or a decrease in friction reduction. The primary objective of the polymer in some oilfield applications, such as hydraulic fracturing, is to maintain a certain level of viscosity to carry proppant (e.g., sand) in the fracture. In other applications, such as slickwater fracturing, the primary objective of the polymer is to provide significant friction reduction while pumping down the wellbore at very high flow rates. It is also desirable to be able to control the viscosity in aqueous compositions having an effective amount of biocide.

In one aspect, the present invention is a method for controlling or arresting the rate of depolymerization of a polymer, typically guar or polyacrylamide, in an application fluid comprising a biocide and a polymer by adding a depolymerization inhibitor to the application fluid. The biocide, in some embodiments, is THMP or a THP salt. It is understood that depolymerization inhibitor and inhibitor may be used interchangeably.

In one aspect, the present invention is a method for preparing a visco-stable application fluid, typically a well treatment fluid, comprising contacting a polymer, typically guar or polyacrylamide, with a depolymerization inhibitor and an effective amount of THPS or tris (hydroxymethyl) phosphine (THMP) or a tetrakis(hydroxymethyl)phosphonium salt (THP salt), typically in an aqueous mixture. The effective amount of THPS or THMP or a THP salt is at or greater than about 20 ppm in one embodiment, at or greater than about 25 ppm in one embodiment, at or greater than about 35 ppm in further embodiments, at or greater than about 50 ppm in other embodiments, at or greater than about 65 ppm in some embodiments, at or greater than about 75 ppm in other embodiments, at or greater than about 100 ppm in other embodiments, at or greater than 15 ppm in other embodiments, while in still other embodiments the effective amount of THPS or THMP or a THP salt is greater than about 1000 ppm, and further in other embodiments greater than about 10,000 ppm. While reference is made to THPS in some aspects/embodiment listed below, it is understood that THMP or THP salt may also be substituted for THPS. It is also understood that THMP, THP salt and THPS can be used interchangeably.

In one embodiment, the biocide is THMP or THP salt, which in a further embodiment is tetrakis(hydroxymethyl) phosphonium sulfate (THPS).

Typically, the depolymerization inhibitor described herein is any material which is water soluble at use concentrations, does not reduce efficacy of the one or more biocides present, and when added to an application fluid containing or eventually containing a polymer and THPS, results in a visco-stable or substantially visco-stable system.

In another embodiment, the depolymerization inhibitor described herein is any material which is water soluble at use concentrations, does not reduce efficacy of the one or more biocides present. When added to an application fluid containing or eventually containing a polymer and THPS, the depolymerization inhibitor maintains or increases friction reduction of an application fluid relative to an application fluid absent the depolymerization inhibitor. Biocides are used in slickwater applications to prevent bacteria growth but may alter the physical characteristics of fluids such as viscosity and friction reduction by degrading the polymer.

In one embodiment, the depolymerization inhibitor can be selected from a suitable radical inhibitor and or an antioxidant. In another embodiment, the depolymerization inhibitor includes hydroquinone, quinone, ascorbic acid, isoascorbic acid, thiols, glutathione, polyphenols, Vitamin A or a combination thereof. In another embodiment, the depolymerization inhibitor includes hydroquinone, quinone, ascorbic acid, isoascorbic acid or any combination thereof. In one embodiment, the depolymerization inhibitor is ascorbic acid or isoascorbic acid. In another embodiment, the dopolymerization inhibitor is hydroquinone. In another embodiment, the dopolymerization inhibitor is quinone. The depolymerization inhibitor as described herein is a compound or group of compounds that is capable of inhibiting or controlling depolymerization even in the presence of or continuous presence and exposure to oxygen. In other words, the application fluid can be in continuous exposure with an oxygen-containing environment, such as air.

In one aspect, described herein are methods for controlling or arresting the rate of depolymerizing of a polymer in a biocide-containing application fluid comprising the step of contacting an application fluid with an effective amount of a depolymerization inhibitor, the application fluid comprising a polymer and, optionally, additional additives.

It is know that THPS is incompatible with sulphite, bisulfite, thiosulfate and thiosulphate-based oxygen scavengers. US 2010/0218950 Describes the choice of a biocide which is compatible with oxygen scavengers such as those based on the soluble salts of sulfites, bisulfites and thiosulfites. Such oxygen scavengers are incompatible with THPS, hydroxymethyl phosphonium based biocides. These oxygen scavengers are added to well stimulation fluids to minimize oxidative damage to additives and reduce equipment corrosion at the elevated temperatures downhole.

The aerobic depolymerization protection achieved by the depolymerzation inhibitor described herein does not require the use of an oxygen scavenger. It may however be used in conjunction with one or more oxygen scavengers.

In another aspect, described herein are methods of controlling the rate of depolymerization of a polymer during a biocide treatment in preparing an oil field application fluid, comprising: (i) contacting a depolymerization inhibitor with an aqueous solution to form an aqueous mixture, wherein the inhibitor is present in an amount of from about 0.01 to about 1000 ppm; (ii) contacting THP salt—in an amount effective to reduce bacteria count in the aqueous mixture—with the aqueous mixture; and (iii) contacting the resulting mixture with a polymer. In some embodiments, step (i) involves contacting, based on total weight of the application fluid or THP salt, less than about 10 wt % of a depolymerization inhibitor with an aqueous solution to form an aqueous mixture, typically less than 7 wt % of a depolymerization inhibitor, more typically less than 5 wt % of a depolymerization inhibitor, based on total weight of application fluid or THP salt respectively. In other embodiments, step (i) involves contacting, based upon total weight of the application fluid or THP salt, less than about 2 wt % of a depolymerization inhibitor with an aqueous solution to form an aqueous mixture, typically less than about 1 wt % of a depolymerization inhibitor, more typically less than about 0.7 wt % of a depolymerization inhibitor, even more typically less than about 0.5 wt % of a depolymerization inhibitor. In still other embodiments, step (i) involves contacting, based upon total weight of the application fluid or THP salt, less than about 0.3 wt % of a depolymerization inhibitor with an aqueous solution to form an aqueous mixture, typically less than about 0.2 wt % of a depolymerization inhibitor, more typically less than about 0.1 wt % of a depolymerization inhibitor.

In one embodiment, the amount of THP salt effective to reduce bacteria count or bacterial activity in the aqueous mixture is greater than about 15 ppm or 20 ppm or 25 ppm or 50 ppm or 75 ppm or 100 ppm or 150 ppm or 250 ppm.

In a further aspect, described herein are methods for controlling or arresting the rate of depolymerization in an application fluid comprising the steps of contacting: —a depolymerization inhibitor; —a biocide; and—a polymer. The resulting application fluid is visco-stable. In one typical embodiment, the addition of the components can be in any order so long as the depolymerization inhibitor is contacted with the polymer prior to or concurrent with the contact of the biocide with the polymer. In one embodiment, the addition of the components can be in any order so long as long as the application fluid remains visco-stable. For example, a depolymerization inhibitor/biocide (dry or aqueous) mixture can be formulated and then such mixture is contacted with a polymer. As another example, a depolymerization inhibitor/polymer mixture (dry, semi-dry or aqueous phase) can be formulated and then such mixture is contacted with a biocide. The polymer can already be part of an application fluid. In other embodiments, the polymer can be in a dry, semi-dry or dispersed phase when contacted with the depolymerization inhibitor/biocide mixture, the resulting mixture then added to an application fluid.

In one embodiment, the amount of THP salt effective to reduce bacteria count in the application fluid is greater than about 50 ppm and the depolymerization inhibitor is present in an amount about 0.01 ppm and about 500 ppm, or between about 0.1 and about 500 ppm, or between about 0.1 and about 400 ppm, or between about 0.2 and about 200 ppm. In another embodiment, the amount of THP salt effective to reduce bacteria count in the aqueous mixture is greater than about 75 ppm and wherein the depolymerization inhibitor is present in an amount between about 0.01 wt % and 5 wt %, based upon total weight of THP salt. In yet another embodiment, the amount of THP salt effective to reduce bacteria count in the aqueous mixture is greater than about 100 ppm, and wherein the depolymerization inhibitor is present in an amount between about 0.1 wt % and about 5 wt %, based upon total weight of THP salt.

In yet another aspect, described herein are wellbore treatment fluids comprising an aqueous medium, a THP salt, a polymer, and a depolymerization inhibitor, wherein the wellbore treatment fluid is visco-stable.

The term "visco-stable" means that viscosity of the aqueous polymer composition or application fluid under certain pressure and temperature can be maintained at a substantially constant level after a predetermined time, which in one embodiment means that the viscosity after such predetermined time ($V_t$) is not less than 45% of an initial viscosity ($V_i$), in other embodiments, not less than 55% of the initial viscosity, in other embodiments, not less than 65% of the initial viscosity, in other embodiments, not less than 70% of the initial viscosity, in other embodiments, not less than 75% of the initial viscosity, in other embodiments, not less than 80% of the initial viscosity, in other embodiments, not less than 85% of the initial viscosity, in other embodiments, not less than 90% of the initial viscosity, and in other embodiments, not less than 95% of the initial viscosity. The predetermined time can vary but is, in some embodiments, 1 minute, 5 minutes, 15 minutes, and 30 minutes, in other embodiments, 60 minutes, in other embodiments, 1 hour, in other embodiments, 2 hours, in other embodiments, 4 hours, in other embodiments, 24 hours, in other embodiments, 4 days, or greater than 5 days. A typical temperature range is 75° F. to 500° F. In another embodiment, the temperature range is from about 100° F. to 400° F. In yet another embodiment, the temperature range is from about 150° F. to about 400° F. Pressure can range from between about 15 psi (pressure per square inch) to about 25,000 psi (pressure per square inch). In typical embodiments, pressure can be up to 20,000 psi. In other embodiments, the pressure can be up to 15,000 psi.

BRIEF DESCRIPTION OF THE DRAWINGS

FIG. 1 shows a table illustrating the effect of depolymerization inhibitors on mixtures of THPS and polyacrylamide.

DETAILED DESCRIPTION

As used herein, the term "alkyl" means a saturated or unsaturated straight chain, branched chain, or cyclic hydrocarbon radical, including but not limited to, methyl, ethyl, n-propyl, iso-propyl, n-butyl, sec-butyl, t-butyl, pentyl, iso-amyl, n-hexyl, and cyclohexyl.

In oilfield applications, natural polymers such as guar or guar derivatives as well as synthetic polymers, mainly polyacrylamides and copolymers containing polyacrylamides, are used in a variety of applications, such as, slickwater fracturing, improving oil recovery (IOR) polymer flooding, enhanced oil recovery (EOR) polymer flooding, fracturing, drilling, cementing, etc. In applications, such as slickwater fracturing, fracturing, etc., it is sometimes desirable to have the polymer maintain a viscosity for a short period of time (for example, 30 minutes to 24 hours, or longer) and then degrade. Other times, it is desirable to have the polymer maintain a viscosity for an extended period of time, for example, greater than about 2 days, or in other embodiments, greater than 3 days, or in yet other embodiments, greater than 4 days, or in yet further embodiments, greater than 5 days.

It is understood that the present invention may be used in a variety of other applications and industrial applications including but not limited to water treatment applications such as process water, e.g. in pulp and paper manufacture, aerobic water systems, water used in hydrostatic testing. The term "application fluid" as used herein includes oilfield application fluids as well as industrial application fluids. Particularly the present invention is suitable in systems and processes where bacteria can proliferate and/or there is a desire or need to control viscosity.

It has been observed that an increase of a biocide, and in particular, tetrakis(hydroxymethyl)phosphonium sulfate (THPS), tris(hydroxymethyl)phosphine (THMP) or a tetrakis(hydroxymethyl)phosphonium salt (THP salt), in an application fluid containing a polymer (e.g, a synthetic or natural polymer) results in a decrease in the viscosity of such fluid.

For example, solutions of polyacrylamide or copolymers of polyacrylamide-co-acrylic acid when mixed with tetrakis (hydroxymethyl)phosphonium sulfate (THPS) at low levels (50-1000 ppm) exhibited a reduction in viscosity along with a corresponding molecular weight reduction. Viscosity is generally related to molecular weight (e.g., Mw) as a lower Mw corresponds to a lower viscosity, compared to a higher Mw, which exhibits a higher relative viscosity. Molecular weight analysis of depolymerization is described in Table 3. Depolymerization can occur at temperatures typical in utilizing such applications, including at room temperature.

The ability to control or arrest the rate of depolymerization in industrial applications such as fracturing in oilfield is desirable, where the high viscosity is desired for a certain period of time and then the viscosity needs to be reduced. This ability is also useful in slickwater fracturing applications in oilfield where high friction reduction using high molecular weight polymers (e.g., polyacrylamides) is important. This ability to control or arrest depolymerization and, thus, control or arrest the loss in viscosity of the application fluid, is very useful in oilfield and well treatment applications.

The ability to control or arrest the rate of depolymerization in industrial applications such as biocide-containing slickwater applications is desirable as depolymerization (of high molecular weight polymers as friction reducers) is correlated to a loss of friction reduction. In slickwater applications in particular, as mentioned above, high friction reduction is important. Some biocides such as THPS, however, appear to have adverse effects on slickwater application fluids, resulting in a loss of friction reduction in such fluids. Thus, a THPS-based biocide-containing slickwater application fluid will generally have lower friction reduction properties than a slickwater application not containing a THPS-based biocide.

Friction reduction is generally described as a percentage friction reduction (% friction reduction), and is defined as the ratio of the decrease in the friction (i.e., pressure drop) while pumping the application fluid (e.g., containing a polymer such as a friction reducing polymer and other additives) compared to the friction (i.e., pressure drop) while pumping solvent (e.g., water) alone.

Thus, the ability to control or arrest depolymerization and, thus, maintain friction reduction in a biocide-containing slickwater application fluid is useful in biocide-containing slickwater applications. It is also useful to maintain an increased friction reduction as compared to biocide-containing slickwater application fluid without a depolymerization inhibitor.

In an embodiment, one test method used to determine the increase of friction reduction of an application fluid, for example, a slickwater application fluid, with the depolymerization inhibitor as described herein as compared to an application fluid without such depolymerization inhibitor is as follows: A loop is filled with a specific amount (e.g., 20 liters) of the application fluid without a biocide (e.g., THPS) and without the depolymerization inhibitor (e.g., hydroquinone, ascorbic acid or isoascorbic acid). The pump is started and a specific flow rate is established and temperature is recorded. The loop is run for a constant time (e.g., one to five minutes) to establish a baseline differential pressure and to make sure no differential pressure anomalies exist. At the end of the period (e.g., one minute), the biocide is slowly added to the recirculation tank. The differential pressure of the application fluid with biocide is recorded at intervals throughout the run. The flow rate should be kept constant, the flow rate of the loop must be continually and quickly returned to its original flow rate. After the run is complete, the loop is cleaned by recirculation of water and confirmed by re-measuring of the differential pressure. A second run is then performed where at the end of period to establish a baseline differential pressure (e.g., one minute), the biocide and depolymerization inhibitor is slowly added to the recirculation tank, attempting to keep the flow rate constant. The differential pressure of the application fluid with biocide and depolymerization inhibitor is then recorded at intervals throughout the second run. The difference of the differential pressure(s) between the first and second run are then evaluated.

In another embodiment, the polymer is guar or a guar derivative. Guar or guar derivatives when mixed with tetrakis(hydroxymethyl)phosphonium sulfate (THPS) at low levels (10-1000 ppm) exhibited a reduction in viscosity of the application fluid along with a corresponding molecular weight reduction. This is generally pronounced when the biocide is in an amount greater than 25 ppm biocide in water. In some embodiments, the reduction in viscosity is observed when the biocide is in an amount greater than 50 ppm biocide in water. In some embodiments, the reduction in viscosity is observed when the biocide is in an amount greater than 75 ppm biocide in water.

In one embodiment, the biocide is THPS or THMP or a THP salt. In one particular embodiment, the THP salt is tetrakis(hydroxymethyl)phosphonium sulphate (THPS). Alternatively, the THP salt may be tetrakis(hydroxymethyl) phosphonium chloride, phosphate, bromide, carbonate, acetate, citrate, formate, lactate, borate or any acceptable salt. The salt is typically the sulphate, chloride or phosphate. However any water soluble salt may be used including the phosphite, bromide, fluoride, carbonate, acetate, formate, citrate, borate, or silicate.

In another embodiment, the biocide is a phosphine or phosphonium compound with 1 or more hydroxyalkyl groups attached to each phosphorus atom. The phosphorus compound may contain one phosphorus atom and may then be of formula $[HORPR'_nO_m]_yX_x$ wherein n is 2 or 3; m is 0 or 1 such that (n+m)=2 or 3; x is 0 or 1 such that (n+x)=2 or 4; y is equal to the valency of X; R is an alkylene group of 1 to 4, typically 1, carbon atoms with the hydroxy group attached to the 1, 2, 3 or 4 numbered carbon atom; each R' may be the same or different and represents an alkyl or alkenyl group, typically of 1-4 carbon atoms, or more usually a group of formula HOR—, wherein R is as defined above; and X is anion such that the phosphorus compound is water soluble. The (—ROH) group may be a 1-, or 2-hydroxyalkyl group, e.g., a hydroxy methyl, 1 or 2 hydroxy ethyl 1 or 2 hydroxypropyl or 1 or 2 hydroxy-butyl group; typically at least one R' is ROH, but may be for example a methyl, ethyl, propyl, iso propyl, or n- sec-, iso- or tert-butyl group. X may be a monovalent anion such as chloride or bromide, or an organic carboxylate, e.g. an alkane carboxylate, typically of 2-5 carbon atoms such as acetate, bisulphite or bisulphate or an organic sulphonate such as methosulphate or a benzene, toluene or xylene sulphonate or a dihydrogen phosphate, or a divalent anion such as sulphate or sulphite or 35 monohydrogen phosphate or a trivalent group such as phosphate or organic carboxylates with 2 or more carboxyl groups such as citrate. The phosphorus compound may also be a phosphine oxide.

The phosphorus compound may alternatively contain 2 or more phosphorus atoms, so long as the phosphorus compound is water soluble to a concentration of at least 0.5 g/1 at 25° C. Such phosphorus compounds contain at least 1 hydroxy alkyl group, usually per phosphorus atom, and typically at least 2 hydroxyalkyl groups per phosphorus atom. Such hydroxyalkyl groups are typically of formula ROH, where R is as defined above. The group or groups joining the phosphorus atoms together may of formula —R—, —R—O—, —R—O—R— or —R—NH—R or —R—R"—R— where R is as defined above and R' is the residue formed by removal of two hydrogen atoms, bonded to nitrogen, from a di or polyamide or di or poly amine, such as urea, dicyandiamide, thiourea or guanidine. Such compounds with 2 or more, e.g. 3, hydroxyalkyl groups per phosphorus atom may be made by self condensation of compounds with 3 or 4 hydroxyalkyl groups attached to one phosphorus atom, e.g. of formula $[HORPR'_nO_m]_yX_x$ or with a compound of formula R"2 such as urea. The condensation can be performed by heating at 40-120° C. Typically, the phosphorus compound contains only one phosphorus atom and 3 or 4 hydroxyalkyl groups especially hydroxymethyl groups. Such compounds are made by reacting phosphine with an aldehyde 50 usually formaldehyde or a ketone in the presence of mineral acid usually hydrochloric, sulphuric or phosphoric acid. Depending on the proportions the product may be a tris hydroxyalkyl phosphine or tetra kis (hydroxyalkyl)phosphonium salt.

Specific examples of biocides include but is understood to be not limited to: tetrakis(hydroxymethyl)phosphonium sulphate, tetrakis(hydroxymethyl)phosphonium chloride, tetrakis(hydroxymethyl)phosphonium phosphate and tris(hydroxymethyl)phosphine oxide as typical examples and dodecyl tris(hydroxymethyl)phosphonium chloride or oleyl tris(hydroxymethyl)phosphonium sulphate. In one embodiment, the biocide is a mixture of two or more biocides from the above list of biocides or biocides as described herein.

In an alternative embodiment, the biocide comprises an alkyl-substituted phosphonium compound of formula (I), and/or an alkyl-substituted phosphine of formula (II):

(I)

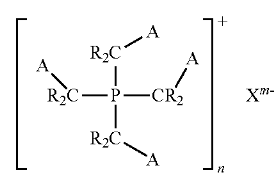

(II)

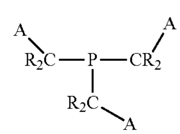

wherein: X is an anion; n is the valency of X represented by m; each A can be the same or different and is selected from OH, OR, SO3R, PO3R2, COOH, COOR, SO3H, PO3H2, CH2COOH, substituted alkyl, aryl and substituted amino groups; each R, and each R, when present, in each A group, is independently selected from hydrogen, a C1 to C20 alkyl, aryl, substituted alkyl or aryl, carboxy or carboxy ester; wherein each CR2 group may be the same or different;

X is selected from chloride, sulphate, phosphate, acetate or bromide.

In another embodiment, the biocide comprises a compound selected from the following:

quaternary ammonium compounds, including but not limited to dodecyl trimethyl ammonium chloride, cetyltrimethylammonium bromide, benzalkonium chloride, didecyldimethylammonium chloride and alkyldimethylbenzylammonium chloride;

polymeric quaternary ammonium compounds, e.g. polyoxyethylene(dimethylimino)ethylene dichloride, among others;

polymeric biguanide hydrochlorides, e.g. polyhexamethylenebiguanide hydrochloride, dodecylguanidine hydrochloride, among others;

tris(hydroxymethyl)nitromethane;
4,4-dimethylozazolidine;
phenoxypropanol;
phenoxyethanol;
glyoxal;
acrolein;

aldehydes, including but not limited to formaldehyde, glutaraldehyde;

triazines, e.g. 1,3,5-tris(2-hydroxyethyl)-1,3,5-hexahydrotriazine, among others;

quaternary phosphonium compounds, e.g. tributyltetradecylphosphonium chloride and tetradecyl tributyl phosphonium chloride, among others;

2-bromo-4-hydroxyacetophenone;

carbamates, e.g. sodium N-dimethyldithiocarbamate, disodium ethylene bisdithiocarbamate, among others;

tertbuthylazine;
tetrachloro-2,4,6-cyano-3-benzonitrile;

thiazole and isothiazole derivatives including but not limited to 2-methyl-4-isothiazolin-3-one, 5-chloro-2-methyl-4-isothiazolin-3-one, 5-chloro-2-methyl-3(2H)-isothiazolone and 1,2-benzisothiazolin-3-one, among others;

compounds with activated halogen groups such as 2-bromo-2-nitro-propan-1,3-diol and 2,2-dibromo-3-nitrilopropionamide, among others;

bis chloromethyl sulphone;
methylene bis thiocyanate; and/or
Na-p-toluensulfonchloroamide, such as Benzenesulfonamide, and N-chloro-4-methyl sodium salt, among others;

Sodium dichloro triazinetrione dehydrate, such as 1,3,5 triazine-2,4,6-(1H,3H,5H)-trione, 1,3-dichloro sodium salt, among others; and/or
chloroamide.

The fluid is typically an oilfield application fluid such as a fracturing fluid, but can encompass any fluid in which a polysaccharide is utilized, including but not limited to slickwater and fracturing fluid. It has been observed that adding THMP or THP salt to a fluid lowers the pH.

It, thus, has been surprisingly discovered that when a polymer such as polyacrylamide is used with THPS under aerobic conditions at acidic pHs, rapid depolymerization occurs. (It is also understood, however, that in other embodiments other biocides aside from THPS can be utilized, including any biocide described herein.) When a depolymerization inhibitor such as ascorbic acid or hydroquinone is added, the depolymerization is controlled or stopped. Suitable depolymerization inhibitors include but are not limited to quinone, hydroquinone, ascorbic acid, isoascorbic acid, thiols, glutathione, polyphenols, or a combination thereof.

Polymers that can be used in connection with the present invention include natural polymers such as polysaccharides, derivatives of natural polymers, synthetic polymers, biopolymers, and the like, or any mixtures thereof.

In one embodiment, the polymer is a synthetic polymer. Synthetic polymers include, but are not limited to, polyacrylamide, poly(methacrylic acid), polyvinylpyrrolidone, poly(acrylic acid), polyacrylate, polyethyleneimine, polyalkylacrylate, poly(ethylene glycol), polypropylene glycol, poly(vinyl alcohol), polyglycerol, polytetrahydrofuran, polyamide, polyglycosans, carboxyalkyl ethers, derivates of or copolymers of any of the foregoing.

The polymers of the present invention can be copolymers. The present invention may employ polymerizable reactive monomers to form a polymer or copolymer. The copolymers may be block copolymers, which include but are not limited to di-block copolymers, tri-block copolymers, comb copolymers or random-block copolymers.

The copolymer can be comprised of blocks, linear backbones, side chains, grafts or branches of microgels or stars, cores of microgels of stars, or parts of polymeric chains having different concentrations of different monomeric units. Thus, the copolymer can include, but is understood not to be limited to, the following structures: (1) block copolymer comprising at least two blocks, part A corresponding to one block, part B corresponding to another block; (2) comb copolymer or grafted copolymer, having a backbone and side chains, with part A corresponding to the backbone and part B corresponding to side chains, or with part B corresponding to the skeleton and part A corresponding to side chains; (3) star copolymer or microgel copolymer or gelled micelle copolymer, comprising a polymeric core or non polymeric core, and peripheral polymeric chains, one part A or B corresponding to the core, and the other part corresponding to peripheral polymeric chains.

In one embodiment, the copolymer is a block copolymer. By block copolymer, it is meant a copolymer comprising at least two different blocks, block A and block B, linked together. The block copolymer is a sequenced polymer, for example a di-block or a tri-block copolymer. Blocks may also be random copolymers. Examples of linear sequences block copolymers are (block A)-(block B) di-block copolymers, (block A)-(block B)-(block A) tri-block copolymers, and (block B)-(block A)-(block B) tri-block copolymers. By linear polymer, it is meant a linear homopolymer, or a linear random copolymer, as opposed to a block copolymer.

A block or part is usually defined by the repeating units it comprises. A block or part may be a copolymer, comprising several kind of repeating units, deriving form several monomers. Hence, block or part A and block or part B may be different polymers, deriving from different monomers, but they may comprise some common repeating units (copolymers).

Examples of units (in part A, for example block A, or in part B, for example block B), derived from monomers include units derived from monomers (but is understood not to be only limited to) of:

alkylesters of an alpha-ethylenically-unsaturated, typically mono-alpha-ethylenically-unsaturated, monocarboxylic acid, such as methylacrylate, ethylacrylate, n-propylacrylate, n-butylacrylate, methylmethacrylate, ethylmethacrylate, n-propylmethacrylate, n-butylmethacrylate, and 2-ethyl-hexyl acrylate, 2-ethyl-hexyl methacrylate, isooctyl acrylate, isooctyl methacrylate, lauryl acrylate, lauryl methacrylate, vinyl versatate,
acrylonitrile,
vinyl nitriles,
vinylamine amides, vinylaromatic compounds such as styrene,
ethylene oxide,
vinyl alcohol,
vinyl pyrrolidone,
acrylamide, methacrylamide,
polyethylene oxide (meth)acrylate (i.e. polyethoxylated (meth)acrylic acid),
hydroxyalkylesters of alpha-ethylenically-unsaturated, typically mono-alpha-ethylenically-unsaturated, monocarboxylic acids, such as 2-hydroxyethylacrylate,
hydroxyalkylamides of alpha-ethylenically-unsaturated, typically mono-alpha-ethylenically-unsaturated, monocarboxylic acids,
dimethylaminoethyl(meth)acrylate, dimethylaminopropyl(meth)acrylate, ditertiobutylaminoethyl(meth)acrylate, dimethylaminomethyl(meth)acrylamide, dimethylaminopropyl(meth)acrylamide,
ethylenimine, vinylamine, 2-vinylpyridine, 4-vinylpyridine,
trimethylammonium ethyl(meth)acrylate chloride, trimethylammonium ethyl(meth)acrylate methyl sulphate, dimethylammonium ethyl(meth)acrylate benzyl chloride, 4-benzoylbenzyl dimethylammonium ethyl acrylate chloride, trimethyl ammonium ethyl(meth)acrylamido (also called 2-(acryloxy)ethyltrimethylammonium, TMAE-AMS) chloride, trimethylammonium ethyl(meth)acrylate (also called 2-(acryloxy)ethyltrimethylammonium, TMAEAMS) methyl sulphate, trimethyl ammonium propyl(meth)acrylamido chloride, vinylbenzyl trimethyl ammonium chloride,
diallyldimethyl ammonium chloride,
ethylene oxide, propylene oxide,
vinyl sulphonic acid, salts of vinyl sulfonic acid,
vinylbenzene sulphonic acid, salts of vinylbenzene sulphonic acid,
alpha-acrylamidomethylpropanesulphonic acid, salts of alpha-acrylamidomethylpropanesulphonic acid,
2-sulphoethyl methacrylate, salts of 2-sulphoethyl methacrylate,
acrylamido-2-methylpropanesulphonic acid (AMPS), salts of acrylamido-2-methylpropanesulphonic acid,
styrenesulphonate (SS),
glycol, glycerol,
aminoalkyl(meth)acrylates, aminoalkyl(meth)acrylamides,
monomers comprising at least one secondary, tertiary or quaternary amine function, or a heterocyclic group containing a nitrogen atom, vinylamine or ethylenimine,
diallyldialkyl ammonium salts, their mixtures, their salts, and macromonomers deriving from therefrom,
dimethylaminoethyl(meth)acrylate, dimethylaminopropyl(meth)acrylate, ditertiobutylaminoethyl(meth)acrylate, dimethylaminomethyl(meth)acrylamide, dimethylaminopropyl(meth)acrylamide, and
ethylenimine, vinylamine, 2-vinylpyridine, 4-vinylpyridine.

In one embodiment, the polymer is any suitable polysaccharide polymer or polysaccharide polymer derivative, typically water soluble or water dispersible ones. Examples of polysaccharide polymers or polysaccharide polymer derivatives include but are not limited to guar gum, guar gum derivatives, cellulose, cellulose derivatives, starch, starch derivatives, locust bean gum, locust bean gum derivatives, xanthan gum, xanthan gum derivatives, and other polysaccharide polymers or polysaccharide polymer derivatives, for example other galactomannan polymers or derivative, for example cassia gum or cationic cassia gum or cassia gum derivatives, or tara gum. In another embodiment, the polysaccharide include amylopectin and amylopectin derivatives; lignocellulose; xylan, arabinoxylan, glucans, xyloglucans, and other plant cell wall hemicelluloses; pectin, inulin, konjac gum; welan gum, and succinoglycans, gellan, levan, pullulan, mannan, mellan, dextran; and mixtures thereof. In one embodiment, the polymer is guar gum (guar). In another embodiment, the polymer is derivatized guar. In yet another embodiment, the polymer is polyacrylamide.

Cellulose ethers for use in the invention include hydroxyethyl cellulose (HEC), hydroxypropyl cellulose (HPC), water soluble ethylhydroxyethyl cellulose (EHEC), carboxymethyl cellulose (CMC), carboxymethylhydroxyethyl cellulose (CMHEC), hydroxypropylhydroxyethyl cellulose (HPHEC), methyl cellulose (MC), methylhydroxypropyl cellulose (MHPC), methylhydroxyethyl cellulose (MHEC), carboxymethylmethyl cellulose (CMMC), hydrophobically modified carboxymethyl cellulose (HMCMC), hydrophobically modified hydroxyethyl cellulose (HMHEC), hydrophobically modified hydroxypropyl cellulose (HMHPC), hydrophobically modified ethylhydroxyethyl cellulose (HMEHEC), hydrophobically modified carboxymethylhydroxyethyl cellulose (HMCMHEC), hydrophobically modified hydroxypropylhydroxyethyl cellulose (HMHPHEC), hydrophobically modified methyl cellulose (HMMC), hydrophobically modified methylhydroxypropyl cellulose (HMMHPC), hydrophobically modified methylhydroxyethyl cellulose (HMMHEC), hydrophobically modified carboxymethylmethyl cellulose (HMCMMC), cationic hydroxyethyl cellulose (cationic HEC) and cationic hydrophobically modified hydroxyethyl cellulose (cationic HMHEC). Typical cellulose ethers are carboxymethyl cellulose and hydroxyethyl cellulose.

Guar derivatives for use in the invention include carboxymethyl guar (CM guar), hydroxyethyl guar (HE guar), hydroxypropyl guar (HP guar), carboxymethylhydroxypropyl guar (CMHP guar), cationic guar, hydrophobically modified guar (HM guar), hydrophobically modified carboxymethyl guar (HMCM guar), hydrophobically modified hydroxyethyl guar (HMHE guar), hydrophobically modified hydroxypropyl guar (HMHP guar), cationic hydrophobically modified hydroxypropyl guar (cationic HMHP guar), hydrophobically modified carboxymethylhydroxypropyl guar (HMCMHP guar) and hydrophobically modified cationic guar (HM cationic guar).

Examples that may be mentioned include cationic polysaccharide derivatives, for instance guar or cellulose derivatives. Cationic polymers functionalized with hydrophobic groups optionally containing a hydroxyl group, may be used. These hydrophobic groups are attached to the main polymer chain via ether bonds. In the case of hydrophobic or non-hydrophobic modified cationic guars, the cationic group is a quaternary ammonium group bearing three radicals, which may be identical or different, chosen from hydrogen, an alkyl radical. The counterion is a halogen, for example chlorine.

Among the cationic guar derivatives that may be mentioned are guar hydroxypropyl trimonium chloride (Jaguar C13S, C14S, or C17, Jaguar Excel and Jaguar C 2000 sold by the company Rhodia Chimie) or hydroxypropyl guar hydroxypropyl trimonium chloride (Jaguar C162 sold by Rhodia). Among the cationic cellulose derivatives that may be used are trimethylammonium-3-propyl cellulose poly(1, 2-oxyethanediyl)-2-hydroxy ether chloride or polyquaternium-10, for instance Polymer JR400 (INPI name: PQ10) sold by the company Amerchol. Nonionic polysaccharide derivatives, for example hydroxypropyl guar, may also be used.

In the case of cationic polysaccharide derivatives, the degree of hydroxyalkylation (molar substitution or MS) is typically between 0 and 2. In one embodiment, the degree of hydroxyalkylation (molar substitution or MS) is between 0 and 1.2. The degree of cationicity (degree of substitution or DS) can be between 0.01 and 0.6. In another embodiment, the degree of substitution or DS can be between 0.01 and 2.

The polymers of the present invention typically have a weight-average molar mass of from 1,000 g/mol to 10,000,000 g/mol, more typically of from about 10,000 g/mol to about 10,000,000 g/mol, depending on their possible and desired degree of polymerization. In one embodiment, the polymers of the present invention have a weight-average molecular weight of 10,000 to 2,000,000 Daltons. In another embodiment, the polymers of the present invention have a weight-average molecular weight of 2,000,000 to 4,000,000 Daltons. In yet another embodiment, the polymers of the present invention have a weight-average molecular weight of 3,000,000 to 7,000,000 Daltons.

The copolymers according to the invention can be obtained by any suitable method, for example by free-radicals polymerization, controlled or not, or by ring-opening polymerization (including anionic or cationic polymerization), or by anionic or cationic polymerization, or by chemical modification of a polymer. Free-radicals polymerizations, referred to as "living" or "controlled" are typical. There are several methods for making block copolymers.

Any of the polymers of the present invention, e.g., polysaccharide or synthetic polymers, can be present in the application fluid from about 0.01% to 50% by weight of the application fluid, typically from about 0.1% to 20% by weight of the application fluid, more typically from about 0.1% to 10% by weight of the application fluid, and most typically 0.1% to 5% by weight of the application fluid.

Although the biocide is typically THPS, THMP or a THP salt, other biocides can be utilized alone or in combination with THPS, THMP or THP salt including but not limited to glutaraldehyde, isothiazolin, a glutaraldehyde/quaternary ammonium compound blend, quaternary amines, tetrahydro 3,5-dimethyl-1,3,5-thiadiazinane-2-thione, nitrilopropionamide, bronopol and the like.

pH buffers may optionally be added to the application fluids and methods described herein. Such pH buffers can be acidic, neutral or basic. The pH buffer is generally capable of controlling the pH from about pH 3 to about pH 12. For example, in a composition for use at pH of about 4-5, an acetic acid-based buffer can be used. In a composition for use at a pH of 5-7, a fumaric acid-based buffer or a sodium diacetate-based buffer can be used. In a composition for use at a pH of 7-8.5, a sodium bicarbonate-based buffer can be used. In a composition for use at a pH of 9-12, a sodium carbonate or sodium hydroxide-based buffer can be used. Other suitable pH buffers can be used, as are known to those skilled in the art.

Typical pH buffers include, for example, fumaric acid, sulfamic acid, citric acid, adipic acid, acetic acid, and/or other pH buffers, more typically sodium bicarbonate. Suitable amounts of pH buffers, when present, are up to 40 parts, typically up to about 20 parts based on 100 parts guar. In one embodiment, suitable amounts of the pH buffer, when present, are 0.1 to 10 parts based on 100 parts guar.

The crosslinking agents utilized in the present invention include but are not limited to copper compounds, magnesium compounds, borax, glyoxal, zirconium compounds, titanium compounds (for example, titanium IV compounds such as titanium lactate, titanium malate, titanium citrate, titanium ammonium lactate, polyhydroxy complexes of titanium, titanium triethanolamine, and titanium acetylacetonate), calcium compounds, aluminum compounds (such as, for example, aluminum lactate or aluminum citrate), p-benzoquinone, dicarboxylic acids and their salts, phosphite compounds and phosphate compounds. In another embodiment, the crosslinking agent is a chemical compound containing a polyvalent ion such as, but not necessarily limited to, boron or a metal such as chromium, iron, aluminum, titanium, antimony and zirconium, or mixtures of polyvalent ions In one embodiment, the crosslinking agent is borax. In another embodiment, the crosslinking agent is a zirconium compound. Zirconium compounds can include but are not limited to zirconium acetyl acetonate, zirconium triisopropylamine, zirconium triisopropylamine lactate, zirconium diisopropylamine, zirconium diisopropylamine lactateis and zirconium (IV) compounds such as zirconium lactate, zirconium lactate triethanolamine, zirconium carbonate, zirconium acetylacetonate, zirconium malate, zirconium citrate, and polyhydroxy complexes of zirconium.

In one embodiment, the polymer (typically in the aqueous polymer composition) can be crosslinked with a crosslinking agent, which results in an increase of viscosity of the fluid typically greater than 50 cP, more typically, greater than about 100 cP, and even more typically greater than 200 cP (@100/sec at the formation temperature). In some embodiments, the resulting viscosity is greater than about 200 cP. The crosslinking agent is typically a zirconium compound or a borax compound, but can be any suitable crosslinking.

The depolymerization inhibitor can be any suitable compound or mixture of compounds that is capable of inhibiting or substantially inhibiting the depolymerization of a polymer (such as polyacrylamide or polysaccharide) in the presence of a biocide, without reducing the efficacy of the biocide utilized in the application fluid. In another embodiment, the depolymerization inhibitor can be any suitable compound or mixture of compounds that is capable of inhibiting or substantially inhibiting the depolymerization of a polymer (such as polyacrylamide or polysaccharide) in the presence of a biocide and oxygen, without reducing the efficacy of the biocide utilized in the application fluid, for example, when the application fluid is continuously or continually exposed to (oxygen-containing) air. In one embodiment, the depolymerization inhibitor does not react with the biocide utilized in the fluid. The depolymerization inhibitor can be a naturally occurring compound or material, or a synthetic compound or material.

In one embodiment, the depolymerization inhibitor is a suitable radical inhibitor, an antioxidant or a combination of both. In another embodiment, the depolymerization inhibitor includes but is not limited to hydroquinone, quinone, ascorbic acid, isoascorbic acid, thiols, glutathione, polyphenols, Vitamin A or a combination thereof. In one particular embodiment, the hydroquinone is an alkylated hydroquinone, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butyl-hydroquinone, 2,5-di-tert-butyl-4-hydroxyanisole, 3,5-di-tert-butyl-4-hydroxyanisole, 3,5-di-tert-butyl-4-hydroxyphenyl stearate or bis(3,5-di-tert-butyl-4-hydroxyphenyl) adipate.

In one embodiment, the depolymerization inhibitor is chosen from sodium formaldehyde sulfoxylate, isoascorbic acid, thioglyerol, thiosorbitol, thiourea, thioglycolic acid, cysteine hydrochloride.

In a further embodiment, the depolymerization inhibitor is a naturally occurring or synthetic anti-oxidant, including but not limited to include butylated hydroxyanisole (BHA), butylated hydroxytoluene (BHT), tert-butylhydroquinone (TBHQ), di-tert-butylhydroquinone (DTBHQ), propyl gallate, sesamol, sesamin, beta-carotene, vitamin E and/or tocopherols. In one embodiment, the depolymerization inhibitor is one or any combination of: butylated hydroxyanisole (BHA); butylated hydroxytoluene (BHT); tert-butylhydroquinone (TBHQ); di-tert-butylhydroquinone (DTBHQ); hydroquinone; and quinone. In another embodiment, the depolymerization inhibitor comprises hydroquinone, quinone, ascorbic acid, isoascorbic acid, thiol, glutathione, polyphenol, vitamin A, retinyl acetate, palmitate, alkylated monophenol, alkylthiomethylphenol, tocopherol, hydroxylated thiodiphenyl ether, an alkylidenebisphenol, an O-benzyl compound, an N-benzyl compound, an S-benzyl compound, hydroxybenzylated malonate, aromatic hydroxybenzyl compound, acylaminophenol or any combination thereof The depolymerization inhibitor can be any suitable phenolic antioxidant or a combination of phenolic antioxidants. In one embodiment, the depolymerization inhibitor is selected from any one, or any combination, of alkylated monophenols, alkylthiomethylphenols, tocopherols, hydroxylated thiodiphenyl ethers, alkylidenebisphenols, O- N- and S-benzyl compounds, hydroxybenzylated malonates, aromatic hydroxybenzyl compounds, and/or acylaminophenols. In one embodiment, the depolymerization inhibitor is selected from alkylated monophenols, hydroxylated thiodiphenyl ethers, alkylidenebisphenols, hydroxybenzylated malonates, aromatic hydroxybenzyl compounds, acylaminophenols or any combination of the foregoing.

Well stimulation and completion (treatment) fluid compositions of the present disclosure can further comprise other additives. Additives are generally included to enhance the stability of the fluid composition itself to prevent breakdown caused by exposure to oxygen, temperature change, trace metals, constituents of water added to the fluid composition, and to prevent non-optimal crosslinking reaction kinetics. The choice of components used in fluid compositions is dictated to a large extent by the properties of the hydrocarbon-bearing formation on which they are to be used. Such additives can be selected from the group consisting of water, oils, salts (including organic salts), crosslinkers, polymers, biocides, corrosion inhibitors and dissolvers, pH modifiers (e.g., acids and bases), breakers, metal chelators, metal complexors, wetting agents, polymer stabilizers, clay stabilizers, scale inhibitors and dissolvers, wax inhibitors and dissolvers, asphaltene precipitation inhibitors, water flow inhibitors, fluid loss additives, chemical grouts, diverters, sand consolidation chemicals, proppants, permeability modifiers, viscoelastic fluids, gases (e.g., nitrogen and carbon dioxide), and foaming agents.

The fluids of the present invention include, but are not necessarily limited to, oilfield fluids such as, for example, well servicing fluids, drilling fluids, slickwater fracturing fluids, fracturing fluids, fracturing gels, completion fluids, hole abandonment fluids, and the like, as well as water injection systems and the like.

The polymer can be in a dry form, semi-dry form (about 0.1% to about 50% water) or in an aqueous mixture. In one embodiment, the semi-dry form is from about 0.1% to about 15% water. In another embodiment, the semi-dry form is from about 0.1% to about 13% water. In another embodiment, the semi-dry form is from about 0.1% to about 10% water. In yet another embodiment, the semi-dry form is from about 0.1% to about 7% water. In another embodiment, the semi-dry form is from about 0.1% to about 5% water.

In one embodiment, the method for controlling or arresting the rate of depolymerizing of a polymer in a biocide-containing application fluid comprises the steps of obtaining an application fluid comprising a polymer, then contacting the application fluid with an effective amount of a depolymerization inhibitor and an effective amount of a biocide. In some embodiments, an effective amount of depolymerization inhibitor means less than about 10 wt % of a depolymerization inhibitor, based on total weight of the application fluid or biocide, typically less than 7 wt % of a depolymerization inhibitor, more typically less than 5 wt % of a depolymerization inhibitor. In other embodiments, an effective amount of depolymerization inhibitor means less than about 3 wt % of a depolymerization inhibitor, based on total weight of the application fluid or biocide, typically less than about 2 wt % of a depolymerization inhibitor with an aqueous solution to form an aqueous mixture, more typically less than about 1 wt % of a depolymerization inhibitor, or less than about 0.7 wt % of a depolymerization inhibitor, or less than about 0.5 wt % of a depolymerization inhibitor. In some embodiments, an effective amount of depolymerization inhibitor means less than about 0.3 wt % of a depolymerization inhibitor, based on total weight of the application fluid or biocide, typically less than about 0.2 wt % of a depolymerization inhibitor, more typically less than about 0.1 wt % of a depolymerization inhibitor.

In some embodiments, the effective amount of depolymerization inhibitor means less than about 10 wt % of a depolymerization inhibitor, based on total weight of the application fluid or biocide, typically less than 7 wt % of a depolymerization inhibitor, more typically less than 5 wt % of a depolymerization inhibitor. In other embodiments, an effective amount of depolymerization inhibitor means less than about 3 wt % of a depolymerization inhibitor, based on total weight of the application fluid or biocide, typically less than about 2 wt % of a depolymerization inhibitor with an aqueous solution to form an aqueous mixture, more typically less than about 1 wt % of a depolymerization inhibitor, or less than about 0.7 wt % of a depolymerization inhibitor, or less than about 0.5 wt % of a depolymerization inhibitor. In some embodiments, an effective amount of depolymerization inhibitor means less than about 0.3 wt % of a depolymerization inhibitor, based on total weight of the application fluid or biocide, typically less than about 0.2 wt % of a depolymerization inhibitor, more typically less than about 0.1 wt % of a depolymerization inhibitor.

In another embodiment, the method for controlling or arresting the rate of depolymerizing of a polymer in a biocide-containing application fluid comprises the steps of obtaining an application fluid comprising a polymer and an effective amount of a depolymerization inhibitor, then contacting the application fluid with an effective amount of a biocide.

In another embodiment, the method comprises contacting an application fluid with a biocide which in an effective amount to reduce bacteria count in the application fluid causes depolymerization of the application fluid and a depolymerization inhibitor selected from the group consisting of hydroquinone, ascorbic acid, isoascorbic acid, a thiol, glutathione, a polyphenol, Vitamin A, alkylated monophenols, alkylthiomethylphenols, tocopherols, hydroxylated thiodiphenyl ethers, alkylidenebisphenols, O- N- and S-benzyl compounds, hydroxybenzylated malonates, aromatic hydroxybenzyl compounds, triazine compounds, benzylphosphonates, and acylaminophenols. The method can comprise contacting the polymer with a mixture of an amount of THP salt effective to reduce bacteria count in an application fluid and at least 0.01 ppm depolymerization inhibitor.

In yet another embodiment, described herein are method for controlling the rate of depolymerizing of a polymer in a biocide-containing application fluid comprising the steps of: —obtaining a mixture comprising (i) a depolymerization inhibitor comprising hydroquinone, quinone, ascorbic acid, isoascorbic acid, thiol, glutathione, polyphenol, vitamin A, retinyl acetate, palmitate, alkylated monophenol, alkylthiomethylphenol, tocopherol, hydroxylated thiodiphenyl ether, an alkylidenebisphenol, an O-benzyl compound, an N-benzyl compound, an S-benzyl compound, hydroxybenzylated malonate, aromatic hydroxybenzyl compound, acylaminophenol or any combination thereof; and (ii) a biocide which, when used in an effective amount to reduce bacteria count, causes depolymerization of a polymer in an application fluid; and then -contacting the mixture with the application fluid comprising a polymer.

In another embodiment, described herein are processes to prepare a visco-stable biocide-containing application fluid, the process comprising the step of contacting at least three components: —a depolymerization inhibitor; —a biocide; and—a polymer. The resulting application fluid is visco-stable. It is understood that the addition of the components can be in any order so long as the application fluid remains visco-stable. In one embodiment, the addition of the components can be in any order so long as the depolymerization inhibitor is contacted with the polymer prior to or concurrent with the contact of the biocide with the polymer. For example, a depolymerization inhibitor/biocide (dry or aqueous) mixture can be formulated and then such mixture is contacted with a polymer. As another example, a depolymerization inhibitor/polymer mixture (dry, semi-dry or aqueous phase) can be formulated and then such mixture is contacted with a biocide. The polymer can already be part of an application fluid. In other embodiments, the polymer can be in a dry, semi-dry or dispersed phase when contacted with the depolymerization inhibitor/biocide mixture, then the resulting mixture added to an application fluid.

In yet another embodiment, the present invention is a method of controlling the rate of depolymerization of a polymer in an aqueous polymer composition comprising: a) obtaining a THPS-water mixture having an amount of THPS greater than about 20 ppm; b) contacting a depolymerization inhibitor to the THPS-water mixture; and c) contacting the resulting mixture with a polymer to form an aqueous polymer composition, whereby the aqueous polymer composition is visco-stable. In certain embodiments, the aqueous polymer composition is at or greater than a first viscosity for a predetermined time, and after such predetermined period of time is at or lower than the first viscosity.

In some embodiments, viscosity after such predetermined time ($V_t$) is not less than 45% of an initial viscosity ($V_i$), in other embodiments, not less than 55% of the initial viscosity, in other embodiments, not less than 65% of the initial viscosity, in other embodiments, not less than 70% of the initial viscosity, in other embodiments, not less than 75% of the initial viscosity, in other embodiments, not less than 80% of the initial viscosity, in other embodiments, not less than 85% of the initial viscosity, in other embodiments, not less than 90% of the initial viscosity, and in other embodiments, not less than 95% of the initial viscosity.

In one embodiment, the polymer in an aqueous polymer composition is then crosslinked with a crosslinking agent, which results in an increase of viscosity of the fluid typically greater than 50 cP, more typically, greater than about 100 cP, and even more typically greater than 200 cP (@100/sec at the formation temperature). In some embodiments, the resulting viscosity is greater than about 200 cP. The crosslinking agent is typically a zirconium compound or a borax compound, but can be any suitable crosslinking agent.

In one embodiment, the polymer in the aqueous polymer composition is then crosslinked with a crosslinking agent, which results in an increase of viscosity of the fluid typically greater than about 100 cP, and typically greater than 200 cP (after 30 minutes at 200° F.). The crosslinking agent is typically a zirconium compound or a borax compound, but can be any suitable crosslinking agent.

In another embodiment, the method includes a) obtaining a THPS-water mixture having an amount of tetrakis(hydroxymethyl)phosphonium sulfate (THPS) greater than about 20 ppm; b) contacting a depolymerization inhibitor with the THPS-water mixture; and c) contacting the resulting mixture with a polysaccharide to form an aqueous polysaccharide composition. By adding a depolymerization inhibitor to the THPS-water mixture or aqueous polysaccharide composition, e.g., application fluid, the initial viscosity of the application fluid can be maintained or remain substantially constant (i.e., visco-stable) for a given period of time. Generally, this period of time is from 0.1 to 48 hours, typically 1 to 24 hours and more typically 2 to 4 hours. In another embodiment, this period of time is from 0.1 to 72 hours. After this period of time, the viscosity of the application fluid substantially decreases to less than about 85% of the initial viscosity, or, in some embodiments, less than about 75% of the initial viscosity, or, in some embodiments, less than about 65% of the initial viscosity, or, in some embodiments, less than about 50% of the initial viscosity or, in some embodiments, less than about 35% of the initial viscosity or, in some embodiments, less than about 30% of the initial viscosity or, in other embodiments, less than about 25% of the initial viscosity.

In other embodiments, described herein are methods for controlling or arresting the rate of depolymerizing of a polymer in a biocide-containing application fluid, or methods for improving friction reducing properties in a biocide-containing application fluid, comprising the steps of: obtaining a mixture comprising (i) a depolymerization inhibitor and (ii) a biocide in an effective amount to reduce bacteria count in an application fluid; and contacting the mixture with the application fluid comprising a polymer. The friction reduction in the resulting application fluid is maintained or increased as compared to an application fluid absent the depolymerization inhibitor. It is understood that the addition of the components can be in any order so long as long as friction reduction in the application fluid is maintained or increased as compared to the application fluid without the depolymerization inhibitor. In one embodiment, the addition of the components can be in any order so long as the depolymerization inhibitor is contacted with the polymer prior to or concurrent with the contact of the biocide with the polymer.

In other embodiments, a friction reducing application fluid containing biocide (in an effective amount to reduce bacteria count in the application fluid) can be prepared, wherein friction reduction in the biocide is maintained at an acceptable level. Biocides are used in slickwater applications to prevent bacteria growth but may alter the physical characteristics of fluids such as viscosity and friction reduction by degrading the polymer. It has been surprisingly found that by formulating an biocide-containing application fluid (e.g., slickwater application fluid) with the depolymerization inhibitor maintains the friction reduction at an acceptable level, which in one embodiment means that the friction reduction in the resulting biocide-containing application fluid (with depolymerization inhibitor) is greater than the biocide-containing application fluid (without depolymerization inhibitor).

In one embodiment, the method of preparing a biocide-containing friction-reducing application fluid (e.g., slickwater application fluid) comprises contacting: —a depolymerization inhibitor; —a biocide; and—a polymer. The mixture can for part of the application (in cases where other components or additives are introduced) or most or all of the application fluid. In the resulting application fluid, friction reduction is maintained or increased as compared to an application fluid absent the depolymerization inhibitor.

In one embodiment, described herein are additive compositions for use in oilfield application fluids (typically a biocide-containing slickwater application fluid) comprising: a) a THP salt or THPS present in an amount from between about 5% to about 85% by weight of the composition; b) a depolymerization inhibitor present in an amount between about 0.01% to about 50% by weight of the composition; and c) optionally, water. The additive composition is capable of reducing bacteria count in the oilfield application. Further, friction reduction in the resulting application fluid is maintained or increased as compared to an application fluid absent the depolymerization inhibitor. In some embodiments, the biocide (including for example THP salt or THPS) is present in an amount from between about 1% to about 80% by weight of the composition, typically from between about 5% to about 75% by weight of the composition. In other embodiments, the biocide (including for example THP salt or THPS) is present in an amount from between about 5% to about 65% by weight of the composition, typically from between about 15% to about 65% by weight of the composition.

Experiments

Experiment 1—

Viscosity of polyacrylamide and guar with THPS and various levels of ascorbic acid or hydroquinone Referring to FIG. 1, polymer A is polyacrylamide; polymer B is underivatised guar.

The table of FIG. 1 illustrates over a period of time the effect of a biocide such as THPS on polyacrylamide and underivatized guar.

Over a period of 60 minutes, the viscosity (@300 rpm(cP) of a THPS—(1%) polyacrylamide aqueous dispersion without a depolymerization inhibitor decreased significantly where at 50 ppm THPS, the viscosity was measured at 9.7 cP (initial viscosity of 23.8 cP); at 75 ppm THPS the viscosity was measured at 7.3 cP (initial viscosity of 23.8 cP); at 100 ppm THPS the viscosity was measured at 3.9 cP (initial viscosity of 23.8 cP); and at 125 ppm THPS the viscosity was measured at 2 cP (initial viscosity of 23.8 cP).

However, over a period of 60 minutes, the viscosity (@300 rpm(cP) (shear rate 500 s-1) of a THPS—(1%) polyacrylamide aqueous dispersion with a depolymerization inhibitor remained substantially stable where at 75 ppm THPS with 25 ppm hydroquinone the viscosity was measured at 14.6 cP (initial viscosity 23.8 cP); at 75 ppm THPS with 50 ppm hydroquinone the viscosity was measured at 17.1 cP (initial viscosity 25.1 cP); at 75 ppm THPS with 200 ppm ascorbic acid the viscosity was measured at 24.5 cP (initial viscosity 27.5 cP); and at 75 ppm THPS with 100 ppm ascorbic acid (rerun) the viscosity was measured at 25.9 cP (initial viscosity 27.5 cP). Similar depolymerization protection is observed with non derivatised guar.

Slickwater-Guar Preparation Procedure

The polymer(s) under investigation were weighed and dissolved in (deionized) DI water to attain a desired concentration (for example, 0.48% w/w guar, 1.0% w/w polyacrylamide). The solution was mixed thoroughly for 1 h to ensure that the polymer had fully or substantially dissolved and the polymer fully hydrated Polymer-THPS Preparation Procedure The polymer solution as prepared above was placed in a 250 ml beaker. Viscosity was measured with an OFITE viscometer (model 900). Initial viscosity was recorded (300 rpm) (at 500 s$^{-1}$) and then an acetic acid/sodium acetate buffer added to achieve a total concentration in the polymer solution of 0.2% w/w. pH and viscosity were recorded and then the depolymerization inhibitor was added. THPS at the concentration being investigated was then added. Viscosity measurements were then made at various time intervals as recorded in the table of FIG. 1.

Experiment 2—

Viscosity of polyacrylamide in presence of THPS/Ascorbic Acid formulation.

Referring to Table 2, below, THPS/Ascorbic Acid formulation formulations were aged from 0 to 7 days at room temperature and tested in polyacrylamide solutions.

TABLE 2

Stability - measured with poly acrylamide (1%) and 107 ppm of formuation

| Time since formulation | | | 0 days Viscosity | | 7 days Viscosity | |
|---|---|---|---|---|---|---|
| Formulation | | | t = 0 mins | t = 60 mins | t = 0 mins | t = 60 mins |
| Inhibitor | Water | THPS | (cP) | (cP) | (cP) | (cP) |
| 0.1 g ascorbic Acid | 30 g | 69.9 g | 24.8 | 24.3 | 27 | 26.7 |
| 0.5 g ascorbic Acid | 30 g | 69.5 g | 25.2 | 25 | 27.1 | 26.1 |
| 1 g ascorbic Acid | 30 g | 69 g | 24.7 | 24.6 | 26.6 | 26 |
| 2 g ascorbic Acid | 30 g | 68 g | 22.2 | 22 | 27 | 26 |
| 5 g ascorbic Acid | 30 g | 65 g | 22.1 | 22 | 26.3 | 25.5 |

Method of Preparation of THPS/Inhibitor Formulation.

The desired amount of inhibitor (see Table 2) was added to THPS (70% w/w) and the resulting mixture allowed to stand for 15 mins. This formulation was then added to a buffered solution of the polymer under investigation (see experiment 1). Viscosity was measured after 1 h and then this experiment was repeated with the formulated THPS/inhibitor after it had been stored for 7 days at ambient temperature.

Experiment 3—

Molecular weight measurements of polymers in the presence of THPS, with and without an inhibitor.

TABLE 3

| Molecular weight determination | | | | | |
|---|---|---|---|---|---|
| THPS (ppm) | Polymer (% w/w) | Inhibitor (ppm) | Polydispersity (Mw/Mn) | Mw (g/mol) | Mn (g/mol) |
| 0 | 1% pol A | 0 | 1.13 | 1,980,000 | 1,760,000 |
| 75 | 1% pol A | 0 | 1.25 | 812,000 | 652,000 |
| 75 | 1% pol A | 1 ppm Ascorbic Acid | 1.22 | 1,770,000 | 1,460,000 |
| 75 | 1% pol A | 10 ppm Ascorbic Acid | 1.25 | 1,840,000 | 1,480,000 |
| 75 | 1% pol A | 50 ppm Ascorbic Acid | 1.19 | 1,890,000 | 1,590,000 |

Method: solutions were made up of THPS/polymer (see method in experiment 1), with and without inhibitor. The samples were left overnight at ambient temperature and then THPS was destroyed by the addition of 10% thiosulfate solution (1 ml of solution added to 9 mls of polymer/THPS solution). MW was then recorded by GPC using light scattering detection. As shown in Table 3, the resulting weight average molecular weight (Mw) of THPS/polymer solution without an inhibitor is approximately half that of the Mw of THPS/polymer solution with an inhibitor after being left overnight.

The present invention, therefore, is well adapted to carry out the objects and attain the ends and advantages mentioned, as well as others inherent therein. While the invention has been depicted and described and is defined by reference to particular embodiments of the invention, such references do not imply a limitation on the invention, and no such limitation is to be inferred. Consequently, the invention is intended to be limited only by the spirit and scope of the appended claims, giving full cognizance to equivalents in all respects.

The invention claimed is:

1. An additive composition for use in oilfield application fluids consisting of:
    a) a THP salt present in an amount from between about 5% to about 85% by weight of the composition;
    b) a depolymerization inhibitor present in an amount between about 0.01% to about 50% by weight of the composition, the depolymerization inhibitor selected from hydroquinone, quinone, ascorbic acid, isoascorbic acid, thiol, glutathione, polyphenol, vitamin A, retinyl acetate, palmitate, alkylated monophenol, alkylthiomethylphenol, tocopherol, hydroxylated thiodiphenyl ether, an alkylidenebisphenol, an O-benzyl compound, an N-benzyl compound, an S-benzyl compound, hydroxybenzylated malonate, aromatic hydroxybenzyl compound, acylaminophenol or any combination thereof; and
    c) one or more additives selected from:
    (i) water;
    (ii) a biocide different from the THP salt wherein the biocide is selected from quaternary ammonium compounds; polymeric quaternary ammonium compounds; polymeric biguanide hydrochlorides; tris(hydroxymethyl)nitromethane; 4,4-dimethylozazolidine; phenoxypropanol; phenoxyethanol; glyoxal; acrolein; aldehydes; triazines; quaternary phosphonium compounds; 2-bromo-4-hydroxyacetophenone; carbamates; tertbuthylazine; tetrachloro-2,4,6-cyano-3-benzonitrile; thiazole, isothiazole and derivatives thereof; compounds with activated halogen groups; bis chloromethyl sulphone; methylene bis thiocyanate; Na-p-toluensulfonchloroamide; sodium dichloro triazinetrione dehydrate; chloroamide; or any combination thereof; and
    (iii) combinations thereof.

2. The additive of claim 1 wherein the THP salt is present in an amount from between about 20% to about 75% by weight of the composition.

* * * * *